(12) United States Patent
Chaudhuri

(10) Patent No.: US 6,699,463 B2
(45) Date of Patent: Mar. 2, 2004

(54) PHOTOSTABLE CATIONIC ORGANIC SUNSCREEN COMPOUNDS WITH ANTIOXIDANT PROPERTIES AND COMPOSITIONS OBTAINED THEREFROM

(75) Inventor: Ratan K. Chaudhuri, Lincoln Park, NJ (US)

(73) Assignee: EM Industries, Hawthorne, NY (US)

( * ) Notice: Subject to any disclaimer, the term of this patent is extended or adjusted under 35 U.S.C. 154(b) by 14 days.

(21) Appl. No.: 10/119,025

(22) Filed: Apr. 10, 2002

(65) Prior Publication Data

US 2003/0198607 A1 Oct. 23, 2003

(51) Int. Cl.⁷ .................. A61K 7/44; A61K 31/215; C07C 69/76; C07C 239/00; C07C 305/00
(52) U.S. Cl. .................. 424/60; 424/70.1; 424/70.9; 514/531; 514/532; 514/538; 560/8; 560/19; 560/20; 560/21; 560/22; 560/37; 560/38; 560/39; 560/41; 564/161; 564/163; 564/164; 564/166; 564/169; 564/182; 558/20; 558/27; 558/28
(58) Field of Search .................. 560/8, 19, 20, 560/21, 22, 37, 38, 39, 41; 564/161, 163, 164, 166, 169, 182; 424/60, 70.1, 70.9; 558/20, 27, 28; 514/532, 534, 538

(56) References Cited

U.S. PATENT DOCUMENTS

| | | | |
|---|---|---|---|
| 3,225,073 A | * 12/1965 | Glabisch et al. ............ 554/91 |
| 3,256,312 A | 6/1966 | Strobel et al. | |
| 3,272,855 A | 9/1966 | Strobel et al. | |
| 3,275,520 A | 9/1966 | Strobel et al. | |
| 3,278,448 A | 10/1966 | Laurer et al. | |
| 3,535,424 A | 10/1970 | Fujimoto et al. | |
| 3,538,226 A | 11/1970 | Ozaki et al. | |
| 3,860,598 A | 1/1975 | Rosenkranz et al. | |
| 3,928,429 A | 12/1975 | El-Chahawi et al. | |
| 4,180,519 A | * 12/1979 | Neel et al. .................. 558/28 |
| 4,284,621 A | 8/1981 | Preuss et al. | |
| 4,335,054 A | 6/1982 | Blaser et al. | |
| 4,429,096 A | * 1/1984 | Schaefer .................. 526/287 |
| 4,457,911 A | 7/1984 | Conner et al. | |
| 4,504,419 A | 3/1985 | Dexter et al. | |
| 4,515,774 A | 5/1985 | Conner et al. | |
| 4,592,906 A | 6/1986 | Baker | |
| 4,613,499 A | 9/1986 | Conner | |
| 4,647,589 A | 3/1987 | Valone | |
| 4,726,942 A | 2/1988 | Lang et al. | |
| 4,797,493 A | 1/1989 | Matsuno, deceased et al. | |
| 4,971,996 A | 11/1990 | Shiraishi et al. | |
| 4,985,237 A | 1/1991 | Matsuno | |
| 5,057,538 A | 10/1991 | Shiraishi et al. | |
| 5,063,243 A | 11/1991 | Cho et al. | |
| 5,124,354 A | 6/1992 | Green | |
| 5,175,340 A | 12/1992 | Forestier et al. | |
| 5,185,370 A | 2/1993 | Backström et al. | |
| 5,218,000 A | 6/1993 | Usherwood et al. | |
| 5,283,352 A | 2/1994 | Backström et al. | |
| 5,294,643 A | 3/1994 | Fuse et al. | |
| 5,326,785 A | 7/1994 | Cho et al. | |
| 5,427,731 A | 6/1995 | Chesna et al. | |
| 5,427,774 A | 6/1995 | Chaudhuri et al. | |
| 5,451,394 A | 9/1995 | Chaudhuri et al. | |
| 5,451,694 A | 9/1995 | Kuhn et al. | |
| 5,478,856 A | 12/1995 | Suzuki et al. | |
| 5,514,711 A | 5/1996 | Kitano et al. | |
| 5,516,839 A | 5/1996 | Ishidoya et al. | |
| 5,538,716 A | 7/1996 | Forestier et al. | |
| 5,601,811 A | 2/1997 | Gallagher et al. | |
| 5,633,403 A | 5/1997 | Gallagher et al. | |
| 5,654,465 A | 8/1997 | Qian et al. | |

(List continued on next page.)

OTHER PUBLICATIONS

CA:74:10323 abs of Farmaco, Edizione Scientifica by Pagani 25(10) pp 727–48 1970.*
CA:126:130750 abs of WO 9639859 Dec. 1996.*
CA:94:99886 abs of Zeitschrift fuer Naturforschung C: Journa of Biosciences by Strak et al 35c(11–12) pp 963–6 1980.*

(List continued on next page.)

Primary Examiner—D. Margaret Seaman
(74) Attorney, Agent, or Firm—Millen, White, Zelano & Branigan, P.C.

(57) ABSTRACT

Compounds of Formula I

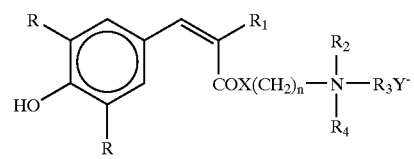

Formula I

Each R is independently linear or branched $C_1$ to $C_8$ alkyl, or linear or branched $C_1$ to $C_8$ alkoxy or one R is H and the other R is linear or branched $C_1$ to $C_8$ alkyl, or linear or branched $C_1$ to $C_8$ alkoxy;

$R_1$ is selected from the group consisting of $COCH_3$, $CO_2R_3$, $CONH_2$, $CONH(R_4)_2$, $CN$, $COX(CH_2)n-N-(R_2)(R_4)(R_3)$, and the quaternized salt form of the formula $COX(CH_2)n-N-(R_2)(R_4)(R_3)^+Y^-$;

X is O or NH;

n is an integer of 1 to 5;

Y is an anion; and $R_2$, $R_3$ and $R_4$ are independently linear or branched $C_1$ to $C_{20}$.

Hair care formulations and other compounds containing compounds of Formula I, and methods for protecting hair and substrates such as polymers, textiles, fabrics, leathers and paints using the compounds herein.

54 Claims, 2 Drawing Sheets

U.S. PATENT DOCUMENTS

| | | |
|---|---|---|
| 5,670,140 A | 9/1997 | Deflandre et al. |
| 5,738,842 A | 4/1998 | Raspanti et al. |
| 5,817,862 A | 10/1998 | Poetsch et al. |
| 5,830,441 A | 11/1998 | Wang et al. |
| 5,888,481 A | 3/1999 | Horn et al. |
| 5,922,310 A | 7/1999 | Chaudhuri et al. |
| 5,951,968 A | 9/1999 | Forestier et al. |
| 6,066,327 A | 5/2000 | Gubernick et al. |
| 6,090,374 A | 7/2000 | Habexk et al. |
| 6,362,146 B1 * | 3/2002 | Macaulay .................. 510/159 |

OTHER PUBLICATIONS

CA:107:102509 abs of Zhongcaoyao by Wang et al 18(3) pp 101–3 1987.*

Wright et al, "Organic NLO Polymers," Marcromolecules, 1994, 27, 3009–3015; published Dec. 1994.

CA 101:85528, Manrao et al., Evaluation of Ferulic Acid Derivatives as Antifungal Agents, pesticides, 1984, 18 (2) 30–36.

* cited by examiner

PHOTOSTABLE CATIONIC ORGANIC SUNSCREEN COMPOUNDS WITH ANTIOXIDANT PROPERTIES AND COMPOSITIONS OBTAINED THEREFROM

BACKGROUND OF THE INVENTION

Photofilters and UV-absorbers have been employed for a number of years to protect coloring dyes from fading from exposure to light. UV-sunscreens have also been employed to protect skin from damage from exposure to sunlight. Representative references related to UV-sunscreens are:

U.S. Pat. No. 5,922,310 (Chaudhuri et al.) discloses a composition which includes a cationic antioxidant phenol in an amount of about 0.01–1% wt/wt.

U.S. Pat. No. 5,427,773 (Chaudhuri et al.); U.S. Pat. No. 5,427,774 (Chaudhuri et al.); and U.S. Pat. No. 5,451,394 (Chaudhuri et al.) discloses non-hydrolysable, non irritating, hair, skin and textile substantive quaternary salts of p-dialkylaminobenzamides.

U.S. Pat. No. 5,633,403 (Gallagher et al.) discloses substantive UV-absorbing cinnamido amine cationic quaternary salts.

U.S. Pat. No. 5,830,441 (Wang et al.) discloses a photostable UV absorbent with maximum absorption above 340 nm.

Hair is largely comprised of polypeptide chains that are held together by disulfide bonds which link adjacent polypeptide chains. The disulfide bonds are largely responsible for the mechanical strength and extensibility of hair. Exposure to sun tends to cause these disulfide bonds to break making the hair stiff and brittle in dry weather and frizzy in humid weather. Additionally, the hair also loses its color and luster in such conditions.

The essential first event in hair photo damage, as in all processes, is light absorption by the fiber. Only wavelengths above 290 nm will be consequential in natural photo damage since shorter wavelength UV light the stratosphere will effectively filter out. The most significant chromophores in proteins that absorb in the UV-B region are the amino acids, tyrosine ($\lambda$max 275 nm), tryptophan ($\lambda$max 280 nm), and the disulfide bonds (weak absorption at 290 nm). The longer wavelength UV-A and the visible light are not likely to cause damage directly since proteins do not absorb them. However, UV-A light is well known for generating free radicals; consequently damage to cholesterol and fatty acids occur.

The photodegradation of hair results in a variety of physical and chemical changes. Among the physical changes are elimination of cuticle cells, roughening of the hair surface, loss of mechanical and elastic strength, and increased porosity. Chemically, we find photooxidation of cysteine, cholesterol, and fatty acids; the decomposition of tryptophan; breakage of disulfide bonds; and bleaching of melanin and artificial hair colors can occur.

Human hair damage caused by sunlight in the UV spectrum is more severe than that resulting from all other factors such as weather, wind, atmospheric pollution, salt water, chlorinated water, perming, coloring, bleaching and improperly applied or repetitive treatments. Sunscreens used for skin are not suitable for hair because they are either not substantive or leave the hair dull and tacky. For hair protection, several approaches have been described, such as the deposition of photofilters on the hair surface, and the use of antioxidants or free radical scavengers.

Recently, sunscreens also have been added to hair care products to guard against the deleterious effects of solar irradiation on the hair. Two sunscreens have been developed especially for hair, Escalol® HP 610 (U.S. Pat. No. 5,451,394) and Incroquat® UV-283 (U.S. Pat. No. 5,633,403). Unfortunately, they both suffer from inadequate photostability, meaning that they degrade in the presence of light, and they lack desired hair substantivity, meaning that they can not be effectively applied and retained on hair.

The ideal sunscreen formulation for hair should be non-toxic and non-irritating to the skin tissue and be capable of convenient application in a uniform and continuous film. The product should be chemically and physically stable so as to provide an acceptable shelf life upon storage. It is particularly desirable that the preparation should retain its protective effect over a prolonged period after application. The product must be substantive to hair or skin so that it does not get washed-off quickly. Thus, the active agent when present on the hair or skin must be resistant to chemical and/or photodegradation and be substantive.

Techniques for stabilizing UV absorbent compositions are known. Representative disclosures in this area include U.S. Pat. Nos. 5,567,418, 5,538,716, 5,951,968 and 5,670,140.

Antioxidants are believed to function by providing protection from free-radical damage. To be an effective free radical quencher, it is believed the antioxidant must be present in an adequate concentration at the site of free radical generation. Since antioxidants are used in low concentrations and typically lack functionality to become substantive to hair or skin, they may not be available at the site of generation, thereby reducing the desired protection. Many existing antioxidants can also act as pro-oxidants instead of antioxidants in presence of iron and copper (see a review on Transition Metal-Induced Oxidation by Chaudhuri and Pucceti, Cosm & Toil, July issue, 2002). Based on these beliefs, it is desirable to provide the antioxidant (having no pro-oxidation activity induced my transition metals) and photostable sunscreen functionality in a single molecule, which is substantive to hair, skin or other substrates to enhance the effectiveness of the antioxidant properties.

SUMMARY OF THE INVENTION

There is provided by the present invention compounds with sunscreen activity, i.e. they are chromophoric within the ultra violet radiation range of from 290–400 nm and they also exhibit antioxidant properties. The sunscreen formulations of this invention preferably offer protection from UV radiation with wavelengths of about 290 nm to 400 nm and preferably from wavelengths in the range of about 290–370 nm.

The compounds of the invention herein are represented by the general Formula I

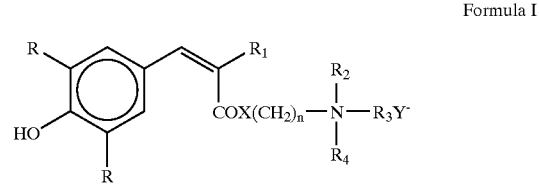

Formula I

In Formula I, each R is independently linear or branched $C_1$ to $C_8$ alkyl, or linear or branched $C_1$ to $C_8$ alkoxy; or one R is H and the other R is linear or branched $C_1$ to $C_8$ alkyl, or linear or branched $C_1$ to $C_8$ alkoxy.

$R_1$ is selected from the group consisting of $COCH_3$, $CO_2R_5$, $CONH_2$, $CONH(R_6)_2$, $CN$, $COX(CH_2)n-N-(R_2)(R_4)(R_3)$, and the quaternized salt form of the formula $COX(CH_2)n-N-(R_2)(R_4)(R_3)^+{}_Y{}^-$;

X is O or NH;

n is an integer of 1 to 5;

Y is an anion;

$R_2$, $R_3$ and $R_4$ are independently linear or branched $C_1$ to $C_{20}$ alkyl; and $R_5$ and $R_6$ are independently hydrogen or linear or branched $C_1$–$C_{20}$ alkyl.

Preferred compounds of Formula I for hair and other substrate protection are illustrated by Formula II Formula II

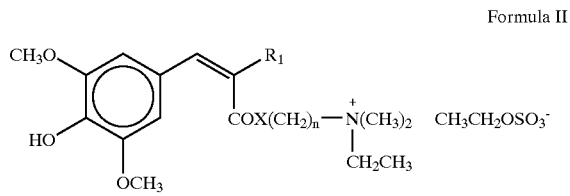

In Formula II, $R_1$ is as defined for Formula I but is preferably $COCH_3$ or $CONH(CH_2)_3N^+(CH_3)_2(CH_2CH_3)$ $CH_3CH_2OSO^-_3$; and X is O or NH.

Concerning Formulae I and II, the integer n is preferably 2 to 3; and the anion Y is preferably Cl, Br, alkyl sulfate, alkyl sulfonate, or p-tolyl sulfonate. $R_2$, $R_3$ and $R_4$ of formulae I and II are preferably independently linear or branched $C_1$ to $C_8$. $R_5$ and $R_6$ are preferably $C_1$ to $C_8$ alkyl.

The invention is also directed to a hair care formulation containing the compound of the invention. The compound is typically used as a protective and conditioning ingredient in the hair care formulation against UV-A rays, UV-B rays, or both against UV-A and UV-B rays. The formulation can contain a single compound of formula I or a mixture of compounds of formula I.

Preferably, the hair care formulation contains a compound or a mixture of compounds of the invention which are substantive and capable of protecting hair, skin or fibers against illumination in the range of about 310 to 360 nm.

It is also preferable that the compound or a mixture of compounds of the invention be capable of stabilizing the hair care formulation against photodegradation, and be further capable of providing an antioxidant property to the formulation.

In another aspect, the invention is directed to a mixture containing at least one compound of the invention and at least one other sunscreen agent. Advantageously, the other sunscreen agent is a sunscreen agent not of Formula I, and the compound of the invention is capable of stabilizing the additional sunscreen agent against photodegradation, or is capable of providing an antioxidant property to the mixture.

In yet another aspect, the invention is also directed to a method of protecting a substrate or an article from UV radiation by applying a compound or mixture of compounds of this invention to the substrate or the article.

Advantageously, the substrate protected from UV radiation is hair. Alternatively, the substrate protected from UV radiation is a polymer, textile fabric, leather or paint. Alternatively, the compound can be used with a hairpiece made of natural or synthetic hair to protect the hairpiece from U.V. degradation.

When the substrate is hair, an amount of the compound sufficient to improve the photostability of the hair care formulation is preferably added, and advantageously, in an amount sufficient to improve the antioxidant activity.

The compounds of this invention can also be used for improving the photostability of a U.V. absorbing composition by adding an effective amount of the compound. Likewise, the antioxidant activity of a composition can be improved by adding an effective amount of a compound of this invention with antioxidant activity. The composition can have one or more compounds of the invention and additional sunscreen agents which are not of the invention.

The sunscreen formulations may contain dispersing agents, emulsifiers or thickening agents to assist in applying a uniform layer of the active compounds. Suitable dispersing agents for the sunscreen formulations include those useful for dispersing organic or inorganic sunscreen agents in either a water phase, oil phase, or part of an emulsion, including, for example, chitosan.

Emulsifiers may be used in the sunscreen formulations to disperse one or more of the compounds or other components of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked CARBOPOL® acrylic polymers from B. F. Goodrich. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/ vinylacetate, PVP/Eicosene copolymer and adipic acids/ diethylene glycol/glycerine crosspolymer etc. Waterproofing agents may be present at levels of from about 0.01 to about 10% by weight.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions preferably has a mean primary particle size of between 5 and 150 nm and preferably from 10 to 100 nm. Titanium oxide may have anatase, rutile or amorphous structure. The zinc oxide in the sunscreen compositions preferably has a mean primary particle size of between 5 nm and 150 nm, preferably between 10 nm and 100 nm. Examples of modified titanium dioxide compositions include (but not limited to only one supplier):

Eusolex® T-45D (surface treated with alumina and simethicone, 45% dispersion in isononoyl isononoate);

Eusolex® T-Aqua, (surface treated with aluminum hydroxide, 25% dispersion in water);

Eusolex® TS (surface treated with aluminum stearate) and

Eusolex® T-2000 and Eusolex® T-ECO (surface treated with alumina and simethicone), all available from MERCK KGaA.

The sunscreen formulation may also contain one or more additional monomeric organic chromophoric compounds. These can either be UV-A, UV-B or broad band filters. Examples of suitable UV-A sunscreens include benzophenone derivatives, menthyl anthranilate, butyl methoxydibenzoyl methane and benzylidene-dioxoimidazoline derivatives. Examples of suitable UV-B sunscreens include cinnamate derivatives, salicylate derivatives, paraaminobenzoic acid derivatives, camphor derivatives, phenylbenzimidazole derivatives and diphenylacrylate derivatives. Examples of suitable broad-band sunscreen include benzotriazole derivatives and triazine derivatives such as anisotriazone. Others include ethylhexyltriazone and diethylhexylbutamidotriazone.

Particularly useful organic sunscreen agents that can be introduced are Avobenzone, 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EM Industries and Merck KGaA, Darmstadt, Germany.

Although not preferred, the sunscreen formulation may contain an additional antioxidant. Examples of suitable antioxidants which provide stability include p-hydroxybenzoic acid and its derivatives (ethylisobutyl, glyceryl esters of p-hydroxybenzoic acid); cumarin derivatives; flavones; hydroxy or methoxy substituted benzophenones; uric or tannic acid and its derivatives; hydroquinones.

In addition to providing sunscreen activity at levels which provide U.V. absorption, the compounds of Formula I can be introduced into a hair care formulation at levels which provide antioxidant activity. It has been found that to provide antioxidant functionality, the phenyl group of the compounds of formula I should have a substituent pattern of "3,5-alkoxy, 4-hydroxy." Compounds of formula I and II also have a moiety which provides UV absorbing functionality, (chromophoric in the UV range).

Additionally, the following compounds can be obtained:

Formula III

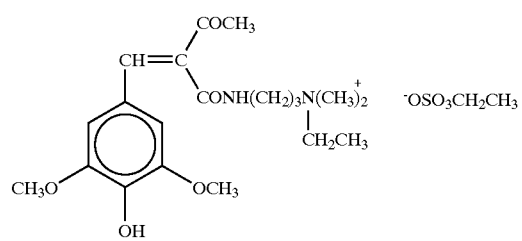

Formula IV

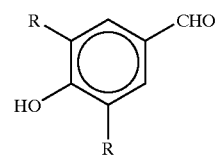

The compounds of Formulae I–IV can be obtained by condensation of a corresponding 3,5-dialkoxy, 4-hydroxy benzaldehyde of the following formula:

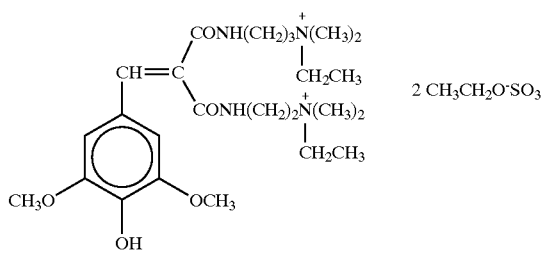

wherein R=linear or branched $C_1$–$C_8$ alkyl or linear or branched $C_1$–$C_8$ alkoxy or one R is H and the other R is linear or branched $C_1$ to $C_8$ alkyl, or linear or branched $C_1$ to $C_8$ alkoxy, with a compound that provides a terminal tertiary amine. An example of a compound that provides a terminal tertiary amine is a compound of the formula: $R_1$—$CH_2$—$C(O)X$ $(CH_2)_n$—$N(R_2)(R_3)$ wherein $R_1$–$R_3$ and X are as defined above for formula I. The tertiary amine is then quarternized with a salt of the formula $(R_4)Y$, wherein $R_4$ is as defined above for formula I. An example of a suitable salt is diethylsulfate $(CH_3CH_2)_2SO_4$.

The corresponding benzaldehyde can be obtained commercially or prepared from 3,4,5-trimethoxybenzaldehyde through selective monodemethylation at the 4-position. This technique leads to syringaldehyde. Alternately, syringaldehyde or other substituted aldehydes can be prepared from 3-bromo-4-hydroxy-5-methoxybenzaldehyde (5-Bromo vanillin) by replacing the bromo atom with methoxy (or alkoxy) using the appropriate alcohol.

Although not wishing to be bound by any specific theory, it is believed that a representative Reaction I resulting in a compound of formula I proceeds in a manner such as this:

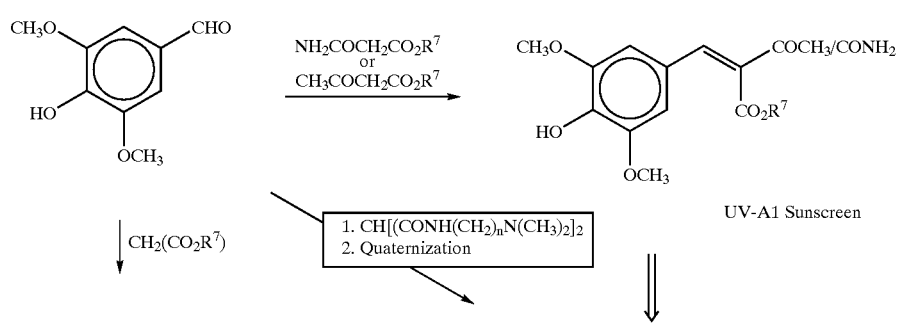

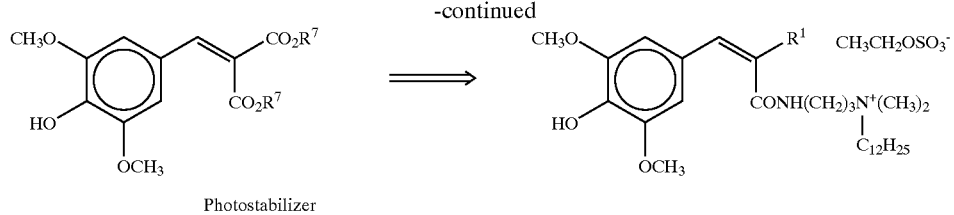

Photostabilizer

Wherein "$R^7$" is $C_1-C_{20}$ linear or branched alkyl, such as ethyl, iso-amyl and ethylhexyl, and $R^1$ is as defined above for formula I.

Similarly, a compound of Formula I has been synthesized from the following representative Reaction II, wherein the condensation step is followed by a quaternization step.

The tertiary amine can be quaternized with diethylsulfate, p-toluene sulfonate or other salts such as $C_{12}H_{25}$ mesylate,

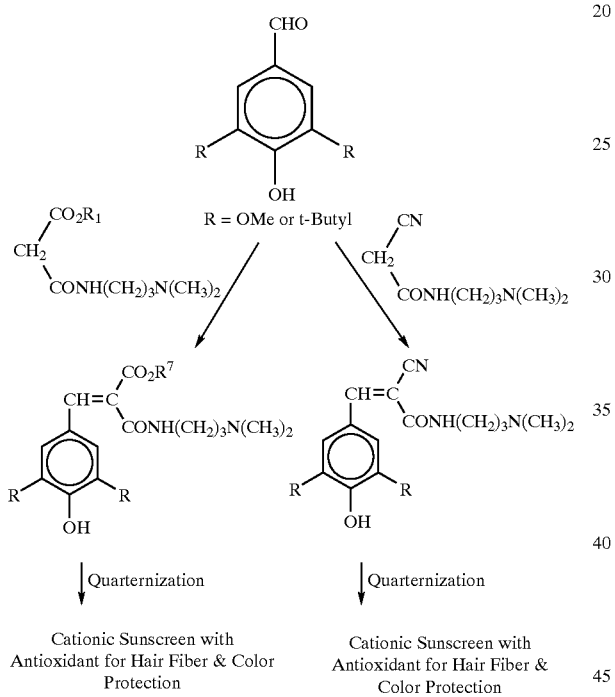

wherein R is as defined above for formula I such as methoxy and t-butyl and $R_7$ is as defined above for Representative Reaction I. An example of a quaternization reaction which provides a compound of formula IV is illustrated below.

The entire disclosure of all applications, patents and publications, cited above are hereby incorporated by reference.

Figure 1:
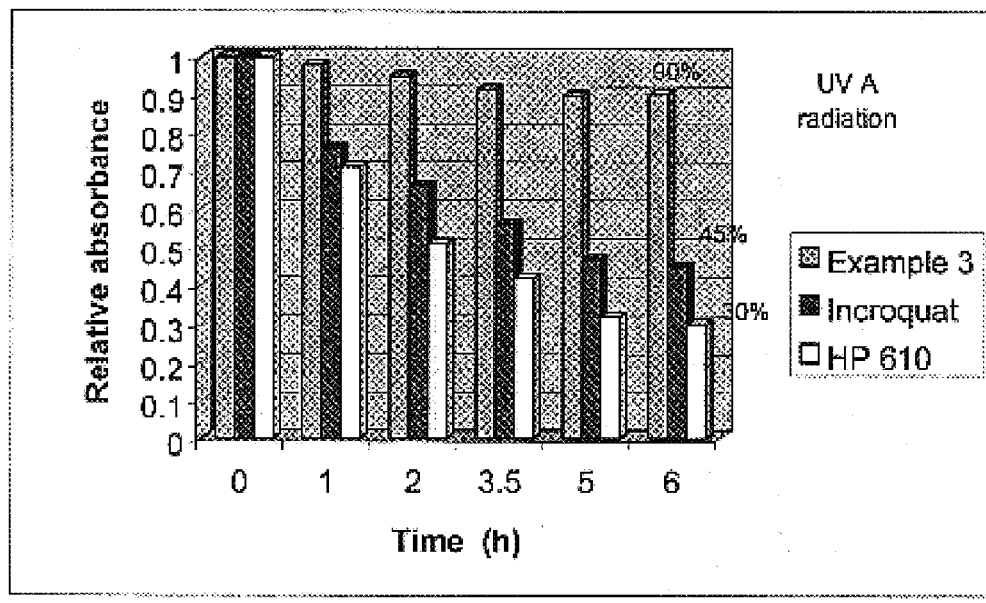
FIG. 1 is a bar graph which illustrates the relative absorbance of UV-A radiation over time by three UV absorbing compounds.

The examples below provide guidelines on how to make representative compounds of the invention.

EXAMPLES

Example I
N-(3-Dimethylaminopropyl)-alpha-acyl-3,5-dimethoxy-4-hydroxy Cinnamide

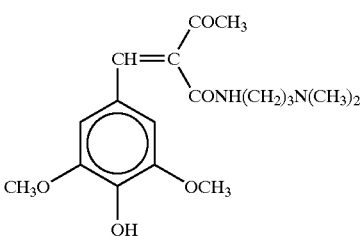

This process is taken in two steps.
1) Selective demethylation
   Momodemethylation of 3,4,5, trimethoxy benzaldehyde is performed using sulphuric acid at 40 degrees for 8 hours. Syringaldehyde is yielded.
2) Condensation
   N,N-Dimethylaminopropyl-alpha-cyanoacetamide is yielded at 80–85% by amidation of ethyl cyanoacetate using dimethyl aminopropylene in neat condition at 90–95° C. 3,5-Dimethyl-4-hydroxy benzaldehyde (Syringaldehyde) is condensed with N,N-Dimethylaminopropyl-alpha-acylacetamide in the presence of piperdine-acetic acid and benzene as media at reflux temperature under continuous azeotropic water removal to yield the title compound. The reaction takes about 2 hours for completion. The yield obtained is about 90%.

The compound is a hair care sunscreen with antioxidant properties and can be quaternized with diethylsulfate to provide a substantive hair care sunscreen with antioxidant properties.

Example 2
N-(3-Dimethyl-3-dodecylaminopropyl)-alpha-cyano-3,5-dimethoxy-4-hydroxy Cinnamide Methane Sulphonate

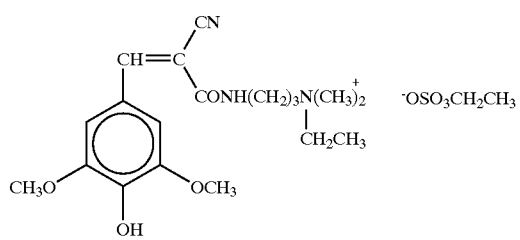

The process involves 3 steps:

1) Selective demethylation

Monodemethylation of 3,4,5, trimethoxybenzaldehyde is performed using sulphuric acid at 40 degrees C. for 8 hours. Syringaldehyde is yielded.

2) Condensation

The N,N-Dimethylaminopropyl-alpha-cyanoacetamide is yielded at 80–85% by amidation of ethyl cyanoacetate using dimethyl aminopropylene in neat condition at 90–95° C. 3,5-diimethoxy-4-hydroxy benzaldehyde is condensed with N.N-Dimethylaminopropyl-alpha-cyanoacetamide in the presence of piperdine-acetic acid and benzene as media at reflux temperature under continuous azeotropic water removal. N-(3-Dimethylaminopropyl)-alpha-cyano-3,5-dimethoxy-4-hydroxycinnamide is yielded. The reaction takes two hours for completion. The yield is 90%.

3) Quaternisation

The N-(3-Dimethylaminopropyl)-alpha-cyano-3,5-dimethoxy cinnamide is quaternised with dodecyl mesylate ($C_{12}H_{25}OSO_2CH_3$) at 100–105 degrees C. in propylene glycol as a reaction medium. The final compound is produced with a 92% yield.

Example 3

Bis-N-[3(N,N-dimethylamino)propyl]-3,5-dimethoxy-4-hydroxybenzylidene Malonamide Bis Ethylsulfate Bis-N-[3(N,N-dimethylamino)propyl]-3,5-dimethoxy-4-hydroxybenzylidene malonamide bis ethylsulfate is prepared by condensation of 3,5-dimethoxy 4-hydroxy benzaldehyde and bis-N-[3-(N,N-dimethylamino)propyl] malonamide according to the following reaction scheme and procedure:

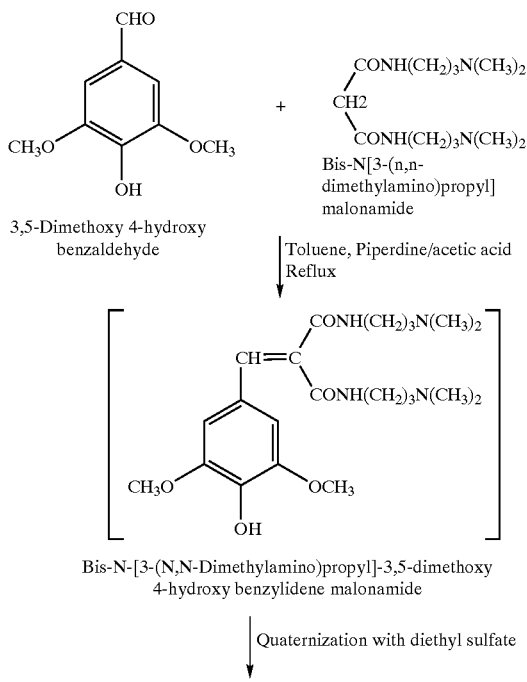

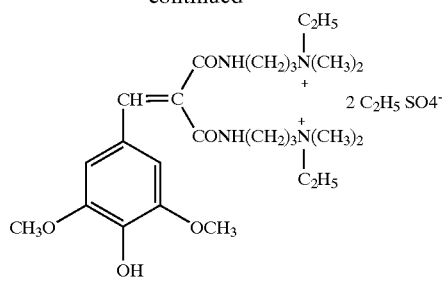

Bis-N-[3-(N,N-Dimethylamino)propyl]-3,5-dimethoxy 4-hydroxy benzylidene malonamide ethyl sulfate Procedure The following are charged with stirring at room temperature: toluene (400.0 ml), syringaldehyde (78.92 gm), bis-N-[3-(N,N-dimethylamino)propyl]malonamide (124.0 gm), piperidine (3.95 ml) and acetic acid (7.90); are heated to reflux temperature and stirred with continuous water removal for 13.5 hours. The reaction was checked by TLC (mobile phase=benzene:hexane:acetone (80:20:10)) with product detected under UV. Once product is detected, the reaction mass is cooled to 60–65 deg. C. and benzene removed under mild vacuum at 60–80 deg. C. The mass is degassed for ½ hour under vacuum at 75–80 deg. C. and nitrogen bleeding is started. The thick residue is dissolved in dimethyl formamide (200.0 ml) with stirring and cooled to 10–15 deg C.

The dissolved reaction mass is charged with diethyl sulphate (150.0 gm) at 10–15 deg C. and is heated to 85–90 deg. C. with stirring for six hours. Benzene (400.0 ml) is charged into this mixture and stirred for 10 minutes at 85–90 deg. C., after which, separate layers were allowed to form. The product layer (lower layer) was separated and washed with benzene (250 ml) at 85–90 deg. C., charged with methanol (350 ml) and charcoal (10.0 gm) at 50–55 deg. C. with stirring for one hour and then filtered through a Hydro-flow bed. The filtered layer was washed with methanol (50 ml) and distilled at 50–55 deg. C. with vacuum to remove methanol.

The mass was degassed for one hour at 90–95 deg. C. under vacuum. The yield obtained is about 85%. The product is highly soluble in water and has $\lambda_{max}$ 323 nm (EtOH:water-70%:30%) with $\epsilon_{max}$=10,500 $cm^{-1}$ $mol^{-1}$. A 50% solution in water was prepared for ease of handling.

Example 4

Bis-N-[3(N,N-dimethylamino)propyl]-3-methoxy-4-hydroxybenzylidene Malonamide Bis Ethylsulfate This material was prepared by following the procedure described in Example 3, except syringaldehyde was replaced with vanillin as a starting material. The product has a $\lambda_{max}$ at 334 nm ($\epsilon$ max 18050 $cm^{-1}$ $mol^{-1}$). A 50% solution in water was prepared for ease of handling.

DPPH Test Method

A DPPH concentrate (2.5×) of 25 mg of 1,1-Diphenyl-2-Picyrl-Hydrazyl ACS#1898-66-4 (Sigma #D-9132, lot 99H3601) dissolved in 250 mL ethanol (USP), is prepared fresh on the measurement date. A DPPH working solution is then prepared by diluting 100 mL of this concentrate to a final volume of 250 mL (100 μM/mL). A blank 13×100 mm borosilicate glass screw top tube of ethanol (USP) is used to zero the spectrometer (Milton Roy, Spectronic 20+) at 517 nm and a control tube of DPPH working solution is measured under identical conditions, and taken as 0% activity.

Aliquots of the 0.25% & 0.5% (RT & 45° C.) test solution are added to tubes followed by the rapid addition of 4 mL DPPH working solution then rapidly capped and mixed. After 20 minutes, the absorbance of each sample is read at 517 nm.

The percent reducing activity (%RA) is calculated using the following equation:

$$\% \text{ Reduction Activity} = 100 \frac{A(0) - A(20)}{A(0)}$$

Where A(0) is the absorbance value of the DPPH working solution at 517 nm zeroed against an ethanol blank and A(20) is the absorbance at 517 nm, 20 minutes after combining the antioxidant with the DPPH working solution.

The concentration of antioxidant (mg/ml) in the final assay mixture is calculated based on the dilution of respective aliquots of each compound in the final assay volume and %RA tabulated and plotted as percent activity at each concentration in the dilution series.

Compounds with 3,5-dimethoxy-4-hydroxy substitution are found to exhibit much higher reducing activity (antioxidant activity) than compounds with 3,4,5-trimethoxy substitution. In order to boost antioxidant activity of the compounds of the present invention, other antioxidants can be combined. Some examples are those antioxidants mentioned above and Tocopherols, tocopherylacetate, Ascorbic acid, Emblica antioxidants, Proanthocyanidins (from pine bark, grape seed extract, and the like) green tea polyphenols, rosemary antioxidants, gallic acid, ellagic acid, butylhydroxy toluene (BHT), butylhydroxy anisole (BHA) and the like. Antioxidant activity of some of the product in the present invention is included in Table A which follows:

TABLE A

| Example | Reductive activity at 30 µg/ml | IC 50% |
|---------|-------------------------------|--------|
| 1 | 23% | 79 µg/ml |
| 2 | 28% | 129 µg/ml |
| 3 | 22% | 118 µg/ml |
| 4 | 8% | 188 µg/ml |

Photostability

The photostability of compounds of the present invention as well as existing commercial cationic sunscreens is tested according to the procedure described below:

Photostability: Comparative Photostability of Example 3, Incroquat® 283 and Escalol® HP610

Three products [Example 3 (1%), Incroquat 283 (1%) and HP610 (0.1%)] were tested for their photostability by dissolving separately in water or ethanol-water solution containing 0.1% Poly(vinylpyrrolidone-vinyl acetate) copolymer (PVP-VA S630 from ISP). Air drying on a glass plate for one hour gave a thin film, which were irradiated under UV A (2 MED/h) and UV B (1 MED/h) light separately over an 8 h period in a Q-UV Accelerated Weathering Tester. Photodegradation was calculated from the decrease in the maximum absorption of the respective products. The results are illustrated in FIGS. 1 and 2.

Figure 2:
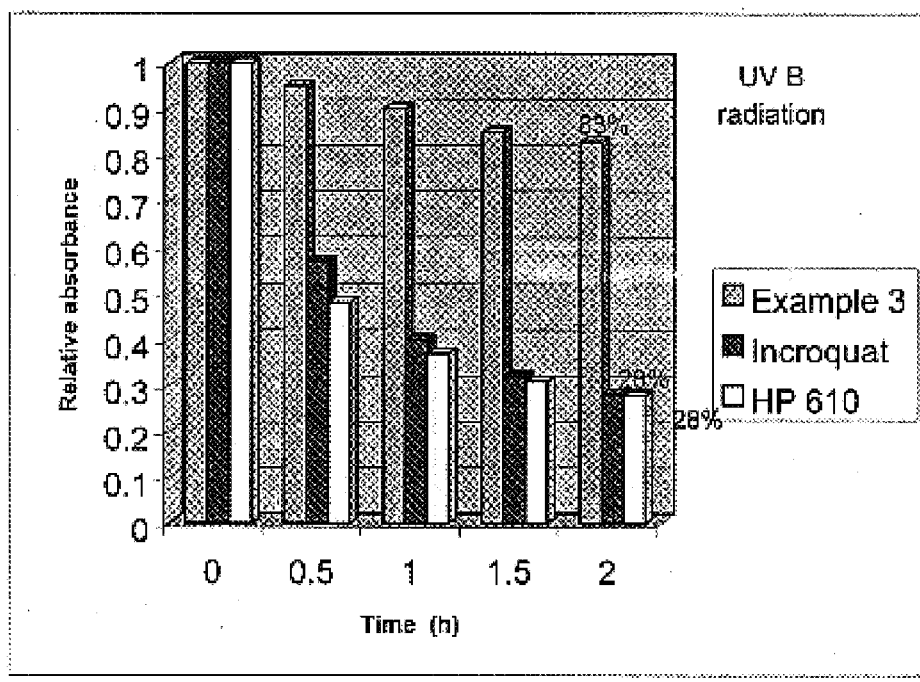
FIG. 2 is a bar graph which illustrates the relative absorbance of UV-B radiation over time by three UV absorbing compounds.

The results in FIGS. 1 and 2 clearly show that the product obtained from Example 3 has much higher photostability over the two commercially available cationic sunscreens, namely, Escalol® HP 610 and Incroquat® UV 283.

Stabilizing Activity

The stabilizing activity of the compound obtained from Example 3 toward Avobenzone is tested and compared with a conventional product according to the procedures below.

Two formulated products [one containing Avobenzone (2%w/w) and the other one with Avobenzone+Example 3 product (2+2% w/w)] were tested for their photostability by applying samples (1–2 µg/cm$^2$) in between two glass plates and irradiating the samples under UV A (2 MED/h) and UV B (1 MED/h) light separately over a 6 hour period in a Q-UV Accelerated Weathering Tester. Photodegradation was calculated from the decrease in the maximum absorption of the respective products. The results show a 54% improvement in photostabilization of Avebenzone using Example 3 product.

Hair Substantivity: Comparative Hair Substantivity of Example 3, Incroquat® 283 and Escalol® HP610

Figure 3:
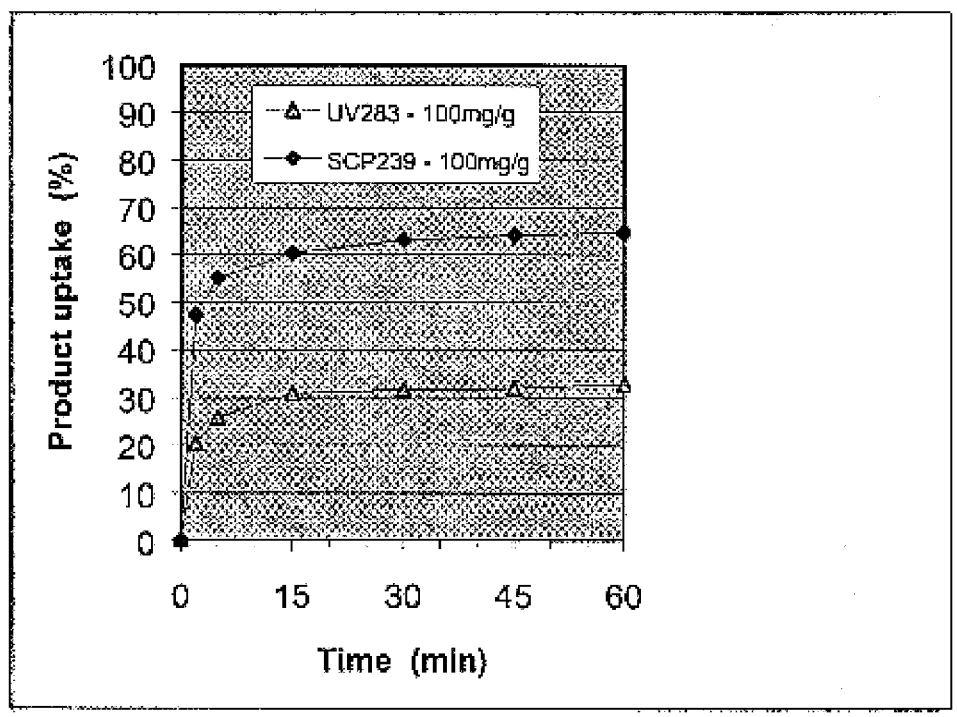
FIG. 3 is graph of product uptake of a hair sample vs. time for two aqueous solutions.

Tests in aqueous solution: Tests are performed by using aqueous solutions of Example 3 (SCP 239) and Incroquat at 1% concentration. 100 ml aqueous solution (containing 100 mg product) are added, under constant stirring, to 1 g of a slightly bleached hair swatch (cut in fine pieces less than ⅓" long). The product uptake is determined by measuring the maximal absorption of product remaining in the solute over time. The results for Example 3 (SCP 239) and Incroquat at 1% concentration are shown in FIG. 3. Escalol® HP610 could not be tested in aqueous solution due to its very poor solubility.

Test in aqueous ethanolic solution: Example 3 (SCP 239) and Incroquat® UV 283 have been prepared in aqueous-ethanolic solution (30:70%) at 1% concentration while a maximal concentration of Escalol® HP610 was reached at 0.25%. 100 ml of each solution is added, under constant stirring, to 1 g of a slightly bleached hair swatch under identical conditions as the previous test. The values for relative uptake of these solutions are reported in FIG. 4.

For better comparison, the relative uptake of Escalol® HP610 is corrected from 0.25% solution to a 1% solution to account for the same initial weight amount as compared to the other two cationic sunscreens (100 mg of initial product present).

Figure 4:
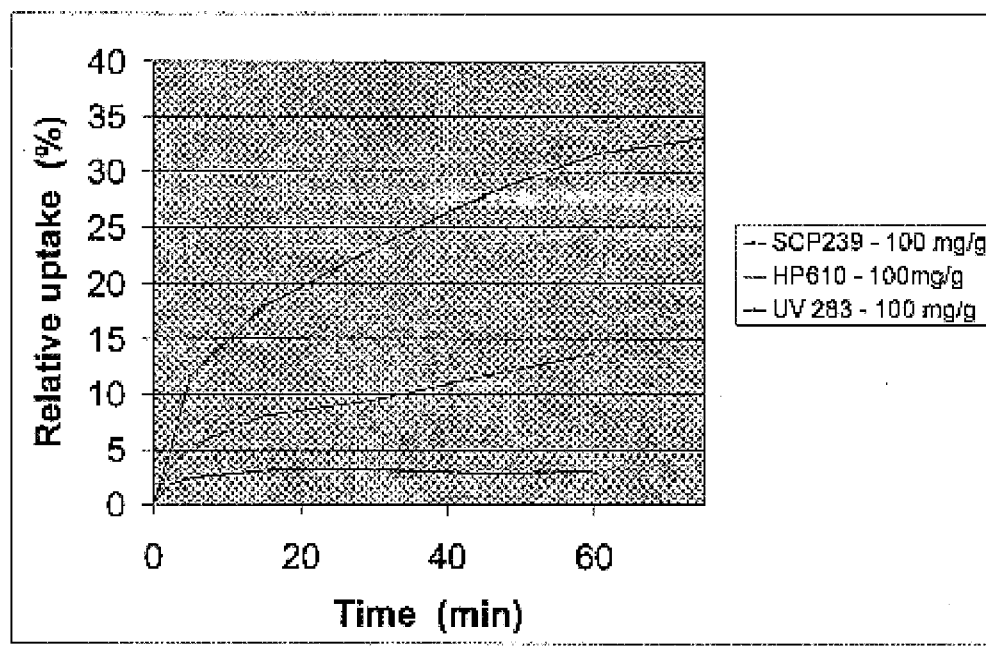
FIG. 4 is graph of product uptake of a hair sample vs. time for three aqueous-ethanolic solutions.

The results illustrated in FIG. 4 clearly show that the product obtained from Example 3 (SCP 239) has much higher hair substantivity from both aqueous and aqueous-ethanolic solutions over two commercially available cationic sunscreens, namely, Escalol® HP 610 and Incroquat® UV 283.

Chelating Property

Iron-catalyzed formation of a hydroxyl radical from a superoxide anion radical and hydrogen peroxide requires the availability of at least one iron coordination site that is either empty or occupied by a readily dissociable ligand, such as water. This coordination with water may be completely displaced by stronger ligands like azide ($N_3^-$) anion. We have applied this principle and determined free coordination site(s) (if any) in the $Fe^{3+}$ (or $Cu^{2+}$)-antioxidant complex using a UV spectrophotometric method (Graf et al, 1984; Martell et al, 1957). The results are recorded in Tables 1 and 2.

TABLE 1

Ultraviolet Spectral Data of $Fe^{3+}$-Chelators*

| | Absorption Maxima of Complex ($\lambda_{max}$ in nm) | |
|---|---|---|
| Chelator/Antioxidant | With $Fe^{3+}$ | $N_3$ Induced Shift |
| EDTA | 241, 283 | 241, 283,410 |
| Example 3 | 249, 321, 403 | 249, 321, 403, No shift |
| Pine Antioxidant | 241, 294, 353, 384 | 241, 294, 353, 400, 440 |
| Vitamin C | 238, 262 | 241, 266, 295 |
| Grape Antioxidant | 247, 295, 353, 396 | 247, 295, 353, 415, 430 |
| Trolox C | 240, 284 | 240, 273, 284, 360 |
| Gallic Acid | 247, 295, 337 | 247, 295, 353, 412 |

*The peak positions are obtained from differential spectroscopic scans of 1.0 mM $Fe^{3+}$ and 5 mM chelator, 1 M $NaN_3$, 50 mM phosphate buffer, pH 7.4, vs. the same solution without sodium azide.

TABLE 2

Ultraviolet Spectral Data of $Cu^{2+}$-Chelators*

| | Absorption Maxima of Complex ($\lambda_{max}$ in nm) | |
|---|---|---|
| Chelator/Antioxidant | With $Cu^{2+}$ | $N_3$ Induced Shift |
| EDTA | 240, 278 | 241, 279, <u>354</u> |
| Example 3 | 249, 324 | 249, 325, No Shift |
| Pine Antioxidant | 239, 279, 302, 331 | 239, 280, 307, <u>430</u> |
| Vitamin C | 239, 263 | 239, 263, <u>284</u>, <u>364</u> |
| Grape Antioxidant | 240, 277, 328 | 240, 277, 328, <u>359</u> |
| Trolox C | 241, 288 | 241, <u>261</u>, <u>352</u>, <u>440</u> |
| Gallic Acid | 240, 258, 321 | 240, 258, <u>331</u>, <u>463</u> |

*The peak positions are obtained from differential spectroscopic scans of 1.0 mM $Cu^{2+}$ and 5 mM chelator, 1 M $NaN_3$, 50 mM phosphate buffer, pH 7.4, vs. the same solution without sodium azide.

Example 3 showed the absence of any water coordination (that is, the complex is fully and firmly saturated and there is no room for any pro-oxidant activity via the formation of oxo-ferryl or oxo-cupryl radical). All other antioxidants/chelators showed disparate coordination site(s) thereby allowed for the formation of oxo-ferryl or oxo-cupryl radicals and manifesting a pro-oxidant effect, particularly at low concentrations. Example 3 as the most effective chelator of loose iron and copper, would prevent oxidative stress-induced damage to hair and skin caused by radicals and loose transition metal ions. Two commercial cationic sunscreens, namely, Escalol® HP 610 and Incroquat® UV 283 do not have iron-or copper-chelating properties. Any iron-or copper-induce oxidative damage to hair, skin or other fibers can not be prevented by these two cationic sunscreens.

Example 5

Shampoo Formulation

| Ingredient | % w/w |
|---|---|
| Phase A | |
| Water, deionized | 85.00 |
| Water, Sodium Laureth Sulfate, Ethoxylated Fatty Alcohol, Sodium Chloride, Sodium Sulfate | 10.00 |
| Water, sodium Chloride, Sodium Glycolate, Cocamido Propylamine, Cocamido Propyl Betaine | 3.00 |
| FD&C Green # 3 or Blue # 1 or Red # 40 (0.1% solution) | 1.00 |
| Phase B | |
| Example 3 or 4/Present Invention | 1.00 |
| Total | 100.00 |

Procedure:
Combine Phase A. Mix until mixture is homogeneous. Add phase B. Mix until mixture is homogeneous.

Example 6

Clear Conditioning Shampoo Formulation

| Ingredient | % w/w |
|---|---|
| Phase A | |
| Water, deionized | 75.00 |
| Sodium Laureth Sulfate (70%) | 14.00 |
| Lauramide DEA | 4.00 |

| Ingredient | % w/w |
|---|---|
| Phase B | |
| Gafquat ® 755 N | 4.00 |
| Panthenol | 1.00 |
| Germaben II | 1.00 |
| Citric acid (25%) | Adjust pH 5–6 |
| Phase C | |
| Example 3 or 4/Present Invention | 2.00 |
| Total | 100.00 |

Procedure:
Combine Phase A and heat to 70° C. Mix until mixture is homogeneous. Add Phase B. Mix until mixture is homogeneous and cool to about 50 C. Add Phase C to the above mixture and stir well. Adjust pH using citric acid to 5–6.

Example 7

Deep Conditioner Formulation With Vegetable Protein

| Ingredient | % w/w |
|---|---|
| Phase A | |
| Water, deionized | 75.50 |
| Phase B | |
| Cetaryl alcohol and Cetareth-20 | 6.00 |
| Cyclomethicone and Dimethiconol and Dimethicone | 1.00 |
| Lauryl Pyrrolidone | 0.50 |
| Phase C | |
| Water, deionized | 10.00 |
| Example 3 or 4/Present Invention | 2.00 |
| Phase C | |
| Propylene glycol and diazolidinyl urea and methyl paraben and propyl paraben | 1.00 |
| Phase D | |
| Hydrolyzed whole wheat protein | 2.00 |
| Phase E | |
| Fragrance as needed | 2.00 |
| Total | 100.00 |

Procedure
Heat Phase A to 70–75 C. with agitation. In a separate vessel, heat Phase B to 70–75 C. until melted. Add B to A with agitation. Cool to 50 C. add Phase C and D with stirring. Allow to cool to room temperature. Then add Phase E, if needed with stirring.

Example 8

Conditioning Color-Enhancer Shampoo Formulation

| Ingredient | % w/w |
|---|---|
| Phase A | |
| Laureth 8 and cocotrimonium chloride and butoxyethanol and PEG-7 glyceryl cocoate and quaternium 80 | 8.00 |

15

-continued

| Ingredient | % w/w |
| --- | --- |
| Phase B | |
| Semi permanent hair dyes | qs |
| Phase C | |
| Water, deionized | qs to 100.00 |
| Phase D | |
| Sodium Laureth sulfate, 28% | 8.00 |
| Phase E | |
| Cocamide DEA | 4.00 |
| Sodium lauroyl sarcosinate | 15.00 |
| Phase F | |
| Example 3 or 4/Present Invention | 2.00 |
| Imidazonyl urea and methylparaben and propyl paraben sodium salt | 0.3 |
| Phase G | |
| Citric acid, to pH 5 to 6 | qs |
| Total | 100.00 |

Procedure
Dissolve Phase B in Phase A under stirring. Heat Phase C to 70–80 C.; add to AB. Add D, then E slowly. When homogeneous, under cooling to about 50 C. add phase F. Adjust pH with citric acid to 5–6.

Example 9

Sun Protection Lotion

| Ingredient | % w/w |
| --- | --- |
| Phase A | |
| Glyceryl stearate citrate | 3.00 |
| Glyceryl laurate/citrate/lactate | 5.00 |
| Caprylic/Capric triglyceride | 16.00 |
| Octylmethoxy cinnamate | 7.00 |
| Microfine Titanium dioxide coated with alumina & simethicone | 3.00 |
| Phase B | |
| Example 3 or 4 | 2.00 |
| Water | 5.00 |
| Phase C | |
| Xanthan gum | 0.50 |
| Preservative | 1.00 |
| Water | Qs to 100.00 |

Procedure
Heat Phase A to approximately to 75 C. Stir Phase B; heat to 75 C. Add B to A with stirring. Homogenize and cool down the temperature to about 50 C. and add Phase C.

The preceding examples can be repeated with similar success by substituting the generically or specifically described reactants and/or operating conditions of this invention for those used in the examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I

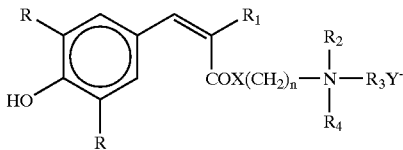

Formula I wherein
each R is independently linear or branched $C_1$ to $C_8$ alkyl, or linear or branched $C_1$ to $C_8$ alkoxy or one R is H and the other R is linear or branched $C_1$ to $C_8$ alkyl, or linear or branched $C_1$ to $C_8$ alkoxy;

$R_1$ is selected from the group consisting of $COCH_3$, $CO_2R_5$, $CONH_2$, $CONH(R_6)_2$, $CN$, and the quaternized salt form of the formula $COX(CH_2)n\text{-}N\text{—}(R_2)(R_4)(R_3)^+Y^-$;

X is O or NH;

n is an integer of 1 to 5;

Y is an anion;

$R_2$, $R_3$ and $R_4$ are independently linear or branched $C_1$ to $C_{20}$ alkyl; and $R_5$ and $R_6$ are independently hydrogen or linear or branched $C_1$–$C_{20}$ alkyl.

2. A compound of Formula II

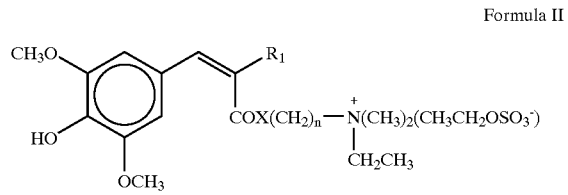

Formula II wherein $R_1$ is selected from the group consisting of $COCH_3$, $CO_2R_5$, $CONH_2$, $CONH(R_6)_2$, $CN$, and the quaternized salt form of the formula $COX(CH_2)n\text{-}N\text{—}(R_2)(R_4)(R_3)^+Y^-$;

$R_2$, $R_3$ and $R_4$ are independently linear or branched $C_1$ to $C_{20}$ alkyl; and $R_5$ and $R_6$ are independently hydrogen or linear or branched $C_1$–$C_{20}$ alkyl, and wherein X is O or NH.

3. A compound of claim 2 wherein $R_1$ is $COCH_3$ or $CONH(CH_2)_3N^+(CH_3)_2(CH_2CH_3)$ $CH_3CH_2OSO^-_3$.

4. A compound of claim 1 wherein X is O.

5. A compound of claim 1 wherein X is NH.

6. A compound of claim 1 wherein the integer n is 2 to 3.

7. A compound of claim 1 wherein the anion Y is selected from Cl, Br, alkyl sulfate, alkyl sulfonate, and p-tolyl sulfonate.

8. A compound of claim 1 wherein $R_4$ is independently linear or branched $C_1$ to $C_8$.

9. A hair care formulation comprised of a compound or a mixture of compounds of claim 2.

10. A hair care formulation comprised of a compound or a mixture of compounds of claim 1 capable of protecting against UV-B or UV-A rays or both UV-A and UV-B rays.

11. A compound of claim 2 wherein X is O.

12. A compound of claim 2 wherein X is NH.

13. A compound of claim 2 wherein the integer n is 2 to 3.

14. A compound of claim 1 wherein the anion Y is an alkyl sulfonate or alkyl sulfate.

15. A hair care formulation comprised of a compound or a mixture of compounds of claim 2 capable of protecting against UV-B or UV-A rays or both UV-A and UV-B rays.

16. A hair care formulation comprised of a compound or a mixture of compounds of claim 1 wherein at least one of the compounds of Formula 1 is capable of stabilizing the formulation against photodegradation.

17. A hair care formulation comprised of at least one compound or a mixture of compounds of claim 1 wherein at least one of the compounds of Formula I is capable of providing an antioxidant property to the formulation.

18. A hair care formulation comprised of a compound or a mixture of compounds of claim 2 wherein at least one of the compounds of Formula II selected is capable of stabilizing the formulation against photodegradation.

19. A hair care formulation comprised of at least one compound or a mixture of compounds of claim 2 wherein at least one of the compounds of Formula II is capable of providing an antioxidant property to the formulation.

20. A mixture comprised of at least one compound of claim 1 and at least one sunscreen agent not of formula I.

21. A mixture comprised of at least one compound of claim 1 and at least one sunscreen agent not of Formula I, wherein the compound of Formula I is capable of stabilizing said at least one sunscreen agent against photodegradation.

22. A mixture comprised of at least one compound of claim 1 with at least one sunscreen agent not of Formula I, wherein the compound of Formula I is capable of providing an antioxidant property to the mixture.

23. A mixture comprised of at least one compound of claim 2 and at least one sunscreen agent not of Formula II, wherein the compound of Formula II is capable of stabilizing the at least one sunscreen agent against photodegradation.

24. A mixture comprised of at least one compound of claim 2 with at least one sunscreen agents not of Formula II wherein the compound of Formula II is capable of providing an antioxidant property to the mixture.

25. A method of protecting a substrate from UV radiation which comprises applying a compound of claim 1 to the substrate.

26. A method as in claim 25 wherein the substrate protected from UV radiation is hair.

27. A method as in claim 25 wherein the substrate protected from UV radiation is selected from the group consisting of polymers, textile fabrics, leathers and paints.

28. A method of protecting a substrate from UV radiation which comprises applying a compound of claim 2 to the substrate.

29. A method as in claim 28 wherein the substrate protected from UV radiation is hair.

30. A method as in claim 28 wherein the substrate protected from UV radiation is selected from the group consisting of polymers, textile fabrics, leathers and paints.

31. A method of improving the photostability of a hair care formulation the method comprising adding a compound of formula I of claim 1 to the formulation in an amount sufficient to improve the photostability of the formulation.

32. A method of improving the antioxidant activity of a hair care formulation the method comprising adding a compound of formula I of claim 1 to the formulation in an amount sufficient to improve the antioxidant activity of the formulation.

33. A method of improving the photostability of a composition comprising sunscreen agents not of Formula I of claim 1 said method comprising adding a compound of formula I of claim 1 to said composition in an amount sufficient to improve the photostability of said composition.

34. A method of improving the antioxidant activity of a composition comprising sunscreen agents not of Formula I of claim 1 said method comprising adding a compound of formula I of claim 1 to said composition in an amount sufficient to improve the antioxidant activity of said composition.

35. A method of improving the photostability of a hair care formulation said method comprising adding a compound of formula II of claim 2 to the formulation in an amount sufficient to improve the photostability of the formulation.

36. A method of improving the antioxidant activity of a hair care formulation said method comprising adding a compound of formula II of claim 2 to the formulation in an amount sufficient to improve the antioxidant activity of the formulation.

37. A method of improving the photostability of a composition comprising sunscreen agents not of Formula II of claim 2 said method comprising adding a compound of formula II of claim 2 to said composition in an amount sufficient to improve the photostability of said composition.

38. A method of improving the antioxidant activity of a composition comprising sunscreen agents not of Formula II of claim 2, said method comprising adding a compound of formula II of claim 2 to said composition in an amount sufficient to improve the antioxidant activity of said composition.

39. An article comprised of at least one compound of claim 1 and a hairpiece.

40. An article comprised of at least one compound of claim 1 with a substrate selected from the group consisting of polymers, textile fabrics, leathers and paints.

41. An article comprised of at least one compound of claim 2 and a hairpiece.

42. An article comprised of at least one compound of claim 2 with a substrate selected from the group consisting of polymers, textile fabrics, leathers and paints.

43. A compound of the following formula:

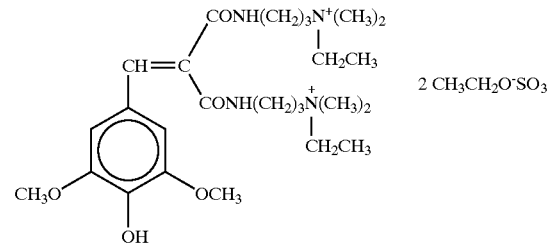

44. A compound of the following formula:

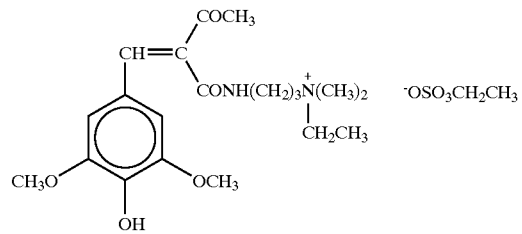

45. A compound of the following formula:

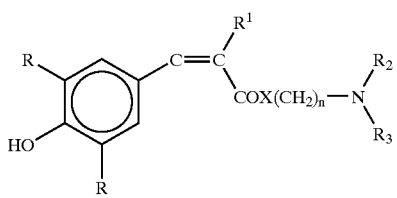

wherein,
each R is independently linear or branched $C_1$ to $C_8$ alkyl, or linear or branched $C_1$ to $C_8$ alkoxy or one R is H and the other R is linear or branched $C_1$ to $C_8$ alkyl, or linear or branched $C_1$ to $C_8$ alkoxy;

R is selected from the group consisting of $COCH_3$, $CO_2R_5$, $CONH_2$, $CONH(R_6)_2$, CN, and the quaternized salt form of the formula $COX(CH_2)n-N-(R_2)(R_4)(R_3)^+Y^-$; X is O or NH;

n is an integer of 1 to 5;

$R_2$, $R_3$ and $R_4$ are independently linear or branched $C_1-C_{20}$ alkyl; and $R_5$ and $R_6$ are independently hydrogen or linear or branched $C_1-C_{20}$ alkyl.

46. A compound of claim 45 wherein X is 0.

47. A compound of claim 45 wherein X is NH.

48. A compound of claim 45 wherein the integer m is 2 to 3.

49. A hair care formulation comprised of a compound or a mixture of compounds of claim 45 capable of protecting against UV-B or UV-A rays or against UV-A and UV-B rays.

50. A mixture comprised of at least one compound of claim 45 and at least one sunscreen agent not of Formula V.

51. A method as in claim 25 wherein the substrate protected from UV radiation is selected from the group consisting of polymers, textile fabrics, leathers and paints.

52. A method of protecting a substrate from UV radiation which comprises applying a compound of claim 45 to the substrate.

53. An article comprised of at least one compound of claim 45 and a hairpiece.

54. A method as in claim 28 wherein the substrate protected from UV radiation are fibers.

* * * * *

UNITED STATES PATENT AND TRADEMARK OFFICE
CERTIFICATE OF CORRECTION

PATENT NO. : 6,699,463 B2
DATED : March 2, 2004
INVENTOR(S) : Ratan K. Chaudhuri It is certified that error appears in the above-identified patent and that said Letters Patent is hereby corrected as shown below:

<u>Column 16,</u>
Line 50, "$CH_3CH_2OSO^-_3$" should be -- $(CH_3CH_2OSO^-_3)$ --.

<u>Column 17,</u>
Line 38, "agents" should be -- agent --.

<u>Column 19,</u>
Line 4, in the structure: "$R^1$" should be -- $R_1$ --.
Line 17, "R is selected" should be -- $R_1$ is selected --.

<u>Column 20,</u>
Line 3, "integer n" should be -- integer m --.
Line 22, "are fibers" should be -- is fibers --.

Signed and Sealed this

Twenty-first Day of June, 2005

JON W. DUDAS
*Director of the United States Patent and Trademark Office*